United States Patent [19]

Hoehn et al.

[11] 4,024,245

[45] May 17, 1977

[54] ANTIBIOTIC A-30912 AND PROCESS FOR PRODUCTION THEREOF

[75] Inventors: Marvin M. Hoehn; Karl H. Michel, both of Indianapolis, Ind.

[73] Assignee: Eli Lilly and Company, Indianapolis, Ind.

[22] Filed: Aug. 25, 1976

[21] Appl. No.: 717,738

Related U.S. Application Data

[63] Continuation-in-part of Ser. No. 619,107, Oct. 2, 1975, abandoned.

[52] U.S. Cl. .............................. 424/119; 195/80 R
[51] Int. Cl.$^2$ ........................................ A61K 35/74
[58] Field of Search .................. 424/119; 195/80 R

[56] References Cited

FOREIGN PATENTS OR APPLICATIONS 568,386  10/1975  Switzerland .................. 424/119

*Primary Examiner*—Jerome D. Goldberg
*Attorney, Agent, or Firm*—Nancy J. Harrison; Arthur R. Whale

[57] ABSTRACT

Antibiotic A-30912 complex, comprising microbiologically active, structurally related factors A, B, C, D, E, F and G, is produced by submerged aerobic fermentation of *Aspergillus rugulosus* NRRL 8113. The A-30912 factors A, B, C, D, E, F, and G are separated from the A-30912 complex by chromatography. The A-30912 complex and individual factors A, B, C, D, E, F, and G are antifungal agents.

9 Claims, 4 Drawing Figures

ANTIBIOTIC A-30912 AND PROCESS FOR PRODUCTION THEREOF

CROSS-REFERENCE TO RELATED APPLICATION

This is a continuation-in-part of copending application Ser. No. 619,107, filed Oct. 2, 1975 now abandoned.

SUMMARY OF THE INVENTION

This invention relates to an antibiotic complex comprising at least 7 individual factors. The complex is produced by culturing a hitherto undescribed strain of the organism *Aspergillus rugulosus* NRRL 8113.

The term "antibiotic complex" as used in the fermentation art and in this specification refers to a mixture of co-produced individual antibiotic factors. As will be recognized by those familiar with antibiotic production by fermentation, the ratio of individual factors produced in an antibiotic complex will vary, depending on the fermentation conditions used.

The antibiotic substances of this invention are arbitrarily designated herein as A-30912 antibiotics. The individual antibiotic factors of the present invention are designated antibiotic A-30912 factors A, B, C, D, E, F, and G.

The A-30912 antibiotic complex is produced by culturing a novel strain of *Aspergillus rugulosus* NRRL 8113 under submerged aerobic fermentation conditions until a substantial level of antibiotic activity is produced. The A-30912 antibiotic complex is extracted from the fermentation medium with polar organic solvents.

The known compound sterigmatocystin is also produced by *Aspergillus rugulosus* NRRL 8113. Sterigmatocystin is extracted either separately with a nonpolar organic solvent or together with the A-30912 antibiotic complex with polar organic solvents. In the latter case, the A-30912 antibiotic complex is separated from sterigmatocystin by concentrating the extracting solvent, adding the concentrate to an excess of a nonpolar organic solvent such as diethyl ether, and separating the A-30912 antibiotic complex as a precipitate. Sterigmatocystin is separated in the filtrate. The A-30912 antibiotic complex is further purified by column chromatography.

The A-30912 antibiotic complex and the individual A-30912 factors are antifungal agents.

DESCRIPTION OF THE DRAWINGS

Infrared absorption spectra of the following A-30912 factors in KBr disc are presented in the accompanying drawings.

A-30912 factor A (Antibiotic A-22082)

Antibiotic A-30912 factor A, a major component of the A-30912 antibiotic complex, is a polypeptide antibiotic. A-30912 factor A is identical to antibiotic A-22082, the subject of a copending application of Higgens and Michel titled ANTIBIOTIC A-22082 AND PROCESS FOR PRODUCTION THEREOF, Ser. No. 619,108, filed Oct. 2, 1975. For convenience, the term antibiotic A-30912 factor A will be used herein to designate this substance. A-30912 factor A is also very similar to the polypeptide antibiotic Echinocandin B recently reported by F. Benz et al., *Helv. Chim. Acta* 57, 2459–2477 (1974) except that Echinocandin B is described as inactive against dermatophytes. A-30912 factor A has good in vitro activity against dermatophytes.

Antibiotic A-30912 factor A is a white amorphous solid. Elemental analysis of A-30912 factor A gave the following percentage composition:

Carbon, 56.52%; hydrogen, 7.29%; nitrogen, 8.68%; oxygen, 27.09%.

The approximate empirical formula proposed for A-30912 factor A is $C_{51-53}H_{79-83}N_7O_{17-19}$. Within this approximate range, the elemental analysis of A-30912 factor A corresponds especially well with an empirical formula of $C_{52}H_{81}N_7O_{18} \cdot H_2O$ (Calcd.: C, 56.24; H, 7.54; N, 8.84; O, 27.39).

A-30912 factor A has an approximate molecular weight of 1100, as determined by mass spectrometry and titration.

Figure 1:
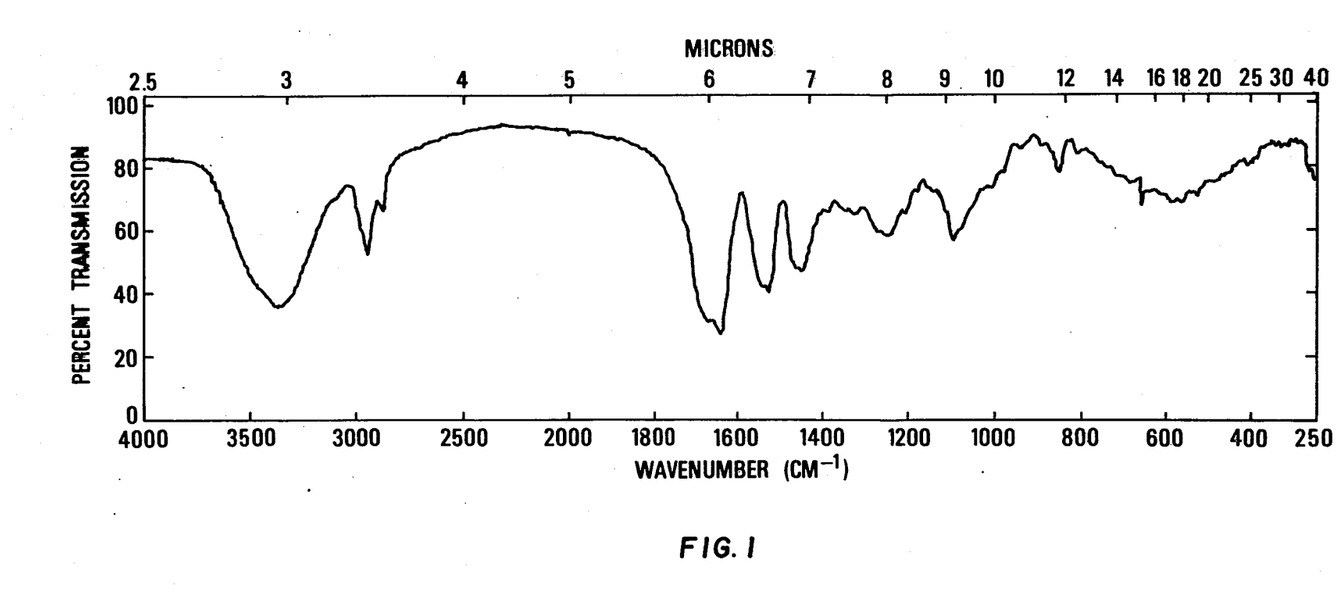
FIG. 1—antibiotic A-30912 factor A.

The infrared absorption spectrum of A-30912 factor A in KBr disc is shown in FIG. 1 of the accompanying drawings. The following characteristic absorption maxima are observed: 2.97 (strong), 3.39 (medium), 3.47 (weak), 5.99 (strong), 6.10 (strong), 6.49 (medium), 6.56 (medium), 6.90 (medium), 8.00 (weak), 9.13 (weak), and 11.77 (weak) microns.

The ultraviolet absorption spectra of A-30912 factor A in both neutral and acidic methanol exhibit absorption maxima at 225 nm ($\epsilon$ 18,000), 275 nm ($\epsilon$ 3,000) and 284 nm (shoulder $\epsilon$ 2,500). The ultraviolet spectrum of factor A in basic methanol shows absorption maxima et 245 nm ($\epsilon$ 16,000) and 290 nm ($\epsilon$ 3,000) and also end absorption.

The $^{13}C$ nuclear magnetic resonance spectrum of A-30912 factor A in perdeuteromethanol shows the following characteristics: δ 176.1, 174.3, 173.4, 172.7, 172.4, 169.8, 158.4, 132.8, 130.9, 129.6, 129.0, 116.2, 77.0, 75.7, 74.4, 71.3, 70.9, 69.6, 68.3, 62.4, 58.7, 56.9, 56.1, 52.9, 39.0, 38.5, 36.8, 35.2, 33.9, 32.9, 32.6, 30.7, 30.4, 30.2, 28.2, 27.0, 26.5, 23.6, 20.1, 19.6, 14.4, and 11.3 ppm.

A-30912 factor A has the following specific rotations:
$[\alpha]_D^{25} -44°$ (c 0.5, $CH_3OH$)
$[\alpha]_{365}^{25} -156°$ (c 0.5, $CH_3OH$)

Electrometric titration of A-30912 factor A in 66% aqueous dimethylformamide indicated the presence of a titratable group with a $pK_a$ value of 12.8 (initial pH 6.9).

Amino-acid analysis of A-30912 factor A indicated the presence, after hydrolysis, of threonine, hydroxyproline and three other as-yet-unidentified amino acids.

Antibiotic A-30912 factor A is soluble in a variety of organic solvents such as methanol, ethanol, dimethylformamide, dimethyl sulfoxide, and ethyl acetate; but is insoluble in nonpolar organic solvents such as diethyl ether and petroleum ether. Antibiotic A-30912 factor A is also soluble in aqueous solutions, especially those having a pH greater than 7.0.

A-30912 Factor D

Antibiotic A-30912 factor D is a white amorphous solid. Elemental analysis of A-30912 factor D gave the following percentage composition: carbon, 56.37 percent; hydrogen, 8.17 percent; nitrogen, 8.54 percent; oxygen (by difference), 26.92 percent.

A-30912 factor D has an approximate molecular weight of 1100, based upon amino-acid analysis and its close structural relationship to A-30912 factor A.

Figure 2:
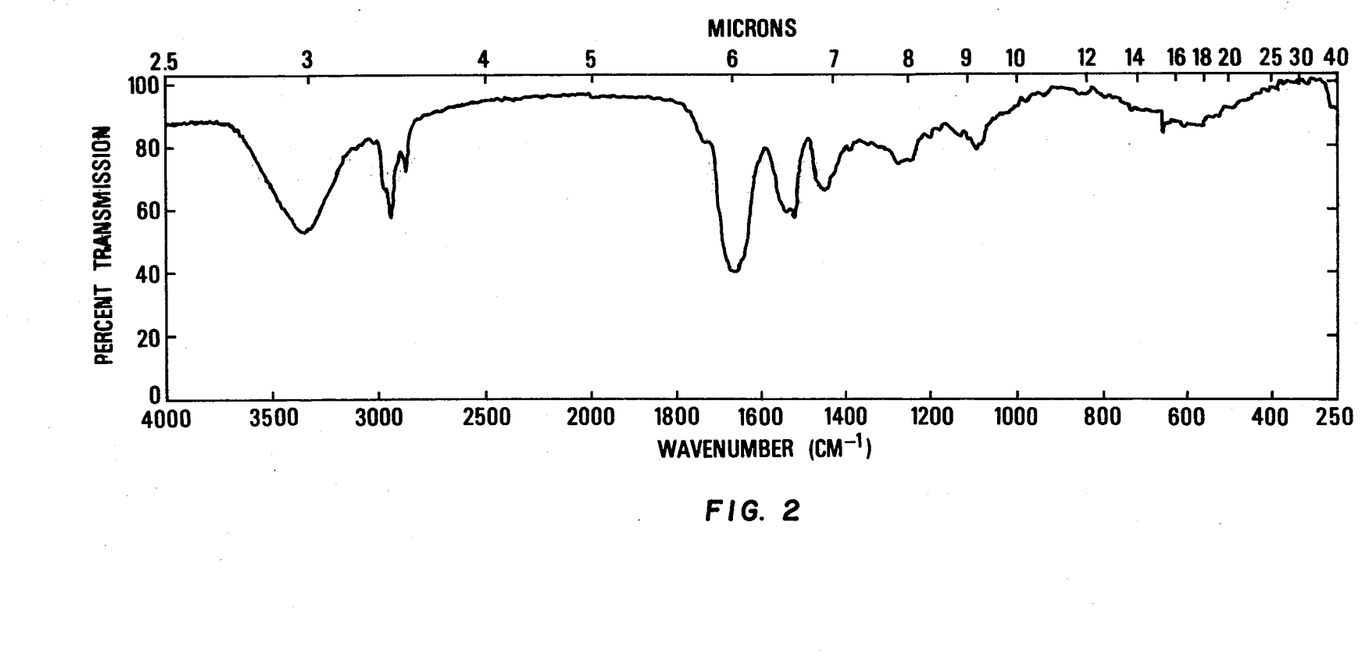
FIG. 2—antibiotic A-30912 factor D.

The infrared absorption spectrum of A-30912 factor D in KBr disc is shown in FIG. 2 of the accompanying drawings. The following characteristic absorption maxima are observed: 2.98 (strong), 3.31 (weak), 3.36 (shoulder), 3.40 (medium), 3.48 (weak), 5.76 (weak), 6.01 (strong), 6.10 (shoulder), 6.49 (medium), 6.57 (medium), 6.90 (medium), 7.81 (weak), 8.07 (weak), and 9.16 (weak) microns.

The ultraviolet absorption (UV) spectra of A-30912 factor D in neutral and acidic methanol exhibit absorption maxima at 225 nm ($\epsilon$ 18,000) and 275 nm ($\epsilon$ 2,500). The UV spectrum of A-30912 factor D in basic methanol exhibits absorption maxima at 240 nm ($\epsilon$ 11,000) and 290 nm ($\epsilon$ 3,000).

A-30912 factor D has the following specific rotation: $[\alpha]_D^{25}$ −50° (c 0.34, $CH_3OH$).

Amino-acid analysis of A-30912 factor D, after hydrolysis, indicated the presence of threonine, hydroxyproline, histidine and three other as-yet-unidentified amino acids. One of the unidentified A-30912-factor-D amino acids is identical to one of the unidentified A-30912-factor-A amino acids.

Antibiotic A-30912 factor D is soluble in a variety of organic solvents such as methanol, ethanol, dimethylformamide, dimethyl sulfoxide, and ethyl acetate; but is insoluble in non-polar organic solvents such as diethyl ether and petroleum ether. A-30912 factor D is soluble in aqueous solutions, especially those having a pH greater than 7.0

A-30912 Factor B

Antibiotic A-30912 factor B is a white amorphous solid. Elemental analysis of A-30912 factor B gave the following approximate percentage composition: carbon, 57.36 percent; hydrogen, 5.92 percent; nitrogen, 8.75 percent; oxygen, 26.19 percent.

Figure 3:
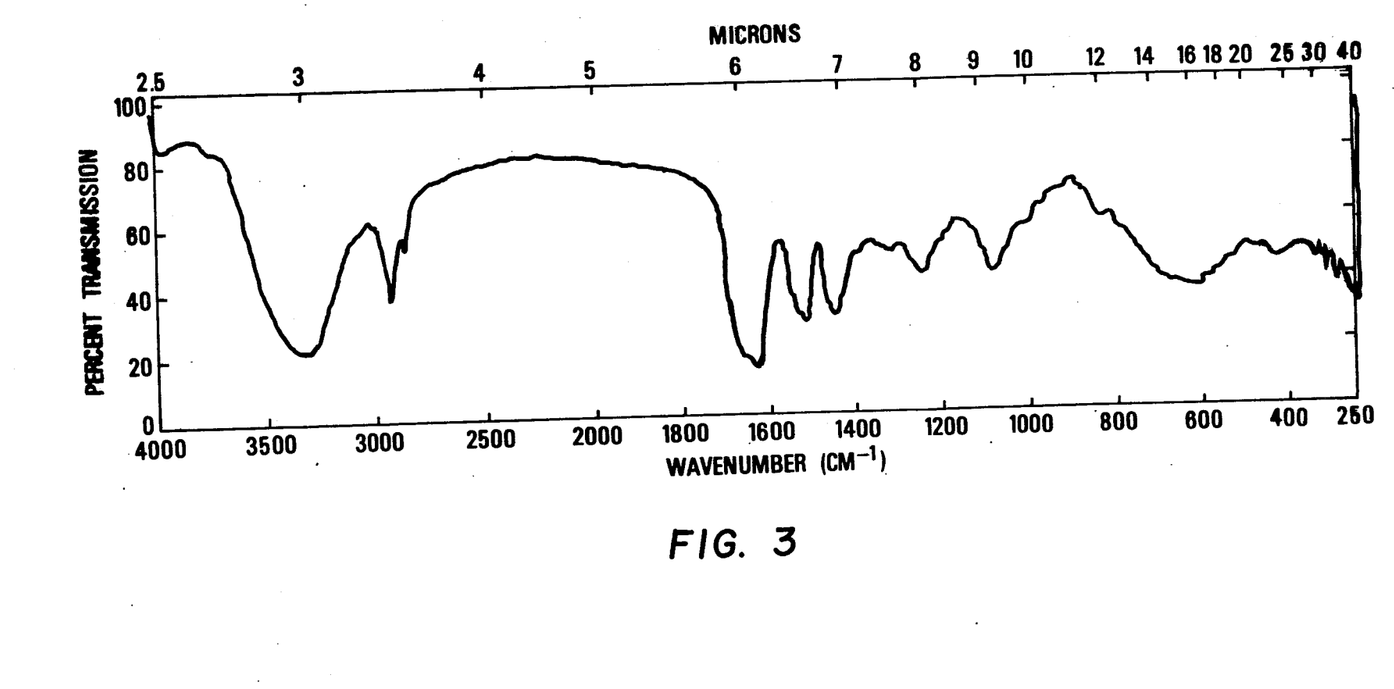
FIG. 3—antibiotic A-30912 factor B.

The infrared absorption spectrum of A-30912 factor B in KBr disc is shown in FIG. 3 of the accompanying drawings. The following characteristic absorption maxima are observed: 2.99, 3.41, 3.49, 6.06, 6.15, 6.54, 6.61, 6.94, 7.62, 8.07, 9.26, and 9.39 microns.

The ultraviolet absorption spectra of A-30912 factor B in both neutral and acidic methanol exhibit absorption maxima at 223 nm (shoulder, $\epsilon$ 16,000) and 278 nm ($\epsilon$ 2,400). The ultraviolet spectrum of antibiotic A-30912 factor B in basic methanol shows absorption maxima at 242 nm ($\epsilon$ 13,900) and 292 nm ($\epsilon$ 2,800).

A-30912 factor B has the following approximate specific rotations:

$[\alpha]_D^{25}$ −47° (c 0.5, $CH_3OH$)
$[\alpha]_{365}^{25}$ −170° (c 0.5, $CH_3OH$).

Electrometric titration of A-30912 factor B in 66% aqueous dimethylformamide indicated the presence of a titratable group with a $pK_a$ value of about 13.0 (initial pH 7.91).

Amino-acid analysis of A-30912 factor B indicated the presence, after standard acid hydrolysis, of threonine, hydroxyproline and several as-yet-unidentified amino acids.

A-30912 factor B is soluble in a variety of organic solvents such as methanol, ethanol, dimethylformamide, dimethyl sulfoxide, and ethyl acetate; but is insoluble in nonpolar organic solvents such as diethyl ether and petroleum ether. A-30912 factor B is also soluble in aqueous solutions, especially those having a pH greater than 7.0.

A-30912 Factor C

Antibiotic A-30912 factor C is a white amorphous solid. Elemental analysis of A-30912 factor C gave the following approximate percentage composition: carbon, 56.76 percent; hydrogen, 7.88 percent; nitrogen, 10.61 percent; oxygen, 25.09 percent.

Figure 4:
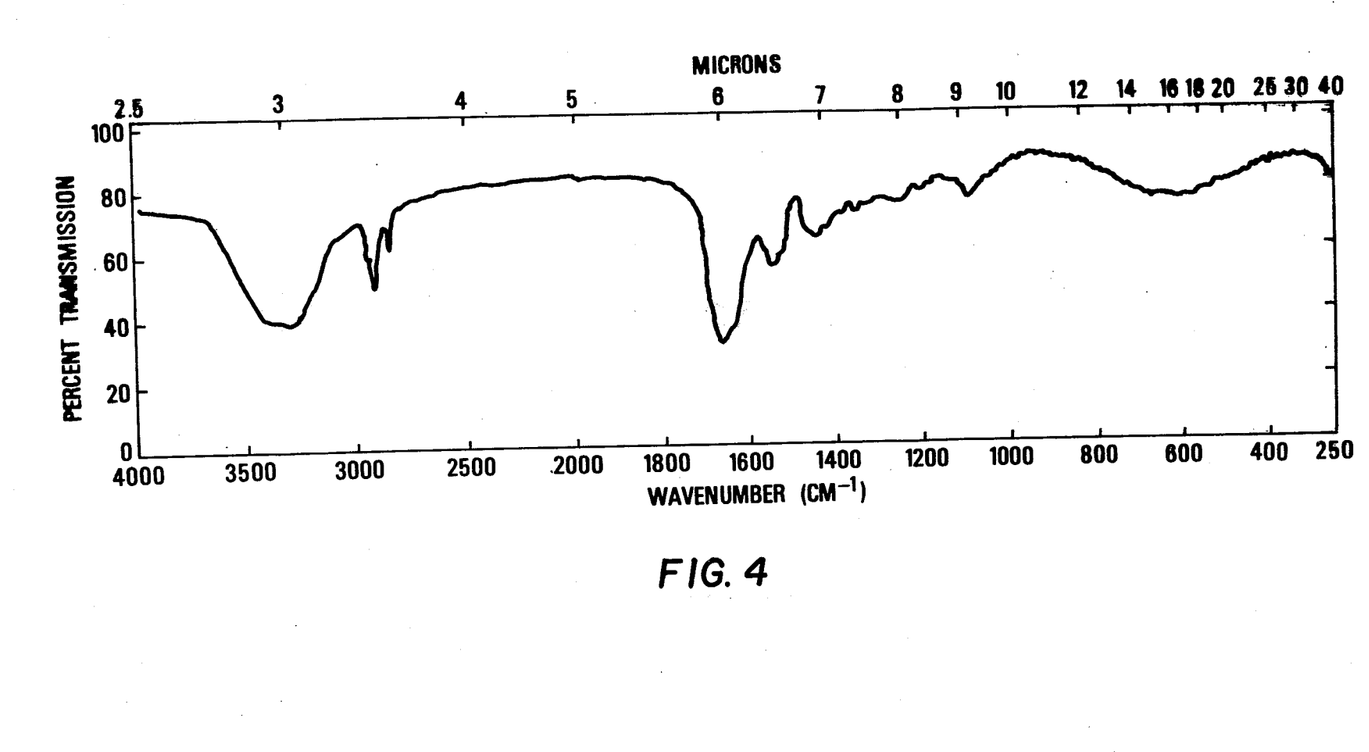
FIG. 4—antibiotic A-30912 factor C.

The infrared absorption spectrum of A-30912 factor C in KBr disc is shown in FIG. 4 of the accompanying drawings. The following characteristic absorption maxima are observed: 2.98, 3.39, 3.43, 3.51, 6.01, 6.12, 6.47, 6.90, 7.04, 7.22, 7.38, 8.00, 8.30, and 9.13 microns.

The ultraviolet absorption spectra of A-30912 factor C in both neutral and acidic methanol exhibit absorption maxima at 223 nm (shoulder, $\epsilon$ 7,300) and 275 nm ($\epsilon$ 1,350). The ultraviolet spectrum of antibiotic A-30912 factor C in basic methanol shows absorption maxima at 240 nm ($\epsilon$ 12,400) and 290 nm ($\epsilon$ 5,200).

A-30912 factor C has the following approximate specific rotations:

$[\alpha]_D^{25}$ − 33° (c 0.5, $CH_3OH$)
$[\alpha]_{365}^{25}$ − 119° (c 0.5, $CH_3OH$).

Electrometric titration of A-30912 factor C in 66% aqueous dimethylformamide indicated the presence of a titratable group with a $pK_a$ value of about 13.08 (initial pH 7.93).

Amino-acid analysis of A-30912 factor C indicated the presence, after standard acid hydrolysis, of threonine, hydroxyproline and several as-yet-unidentified amino acids.

A-30912 factor C is soluble in a variety of organic solvents such as methanol, ethanol, dimethylformamide, dimethyl sulfoxide, and ethyl acetate; but is insoluble in nonpolar organic solvents such as diethyl ether and petroleum ether. A-30912 factor C is also soluble in aqueous solutions, especially those having a pH greater than 7.0.

The seven individual factors of the A-30912 complex can be separated and identified by the use of thin-layer chromatography (TLC). Silica gel is a preferred adsorbent; and benzene:methanol (7:3, V:V) is a preferred solvent system.

The $R_f$ values of A-30912 factors A–G, using silica gel (Merck, Darmstadt) TLC, the benzene:methanol (7:3) solvent system, and Candida albicans bioautography are given in Table I.

TABLE I

| A-30912 Factor | $R_f$ Value |
|---|---|
| A | 0.35 |
| B | 0.45 |
| C | 0.54 |
| D | 0.59 |
| E | 0.27 |
| F | 0.18 |
| G | 0.13 |

The $R_f$ values of A-30912 factor A in various paper-chromatographic systems, again using Candida albicans as a detection organism, are given in Table II.

TABLE II

| A-30912 Factor A R_f Value | Solvent system |
|---|---|
| 0.76 | Butanol saturated with water |
| 0.69 | Butanol saturated with water plus 2% p-toluenesulfonic acid |
| 0.75 | Methanol:0.1 N HCl (3:1) |
| 0.17 | Butanol:ethanol:water (13.5:15:150) |
| 0.78 | Methanol:0.05 M sodium citrate at pH 5.7 (7:3) paper buffered with 0.05 M sodium citrate at pH 5.7 |

The organism useful for the preparation of the A-30912 antibiotic complex was isolated from a soil sample from the ruins of Pompeii, Italy. The A-30912 producing organism is classified as a strain of *Aspergillus rugulosus* Thom and Raper, which is in the *Aspergillus nidulans* form group. This classification is based on the description of K. B. Raper and D. I. Fennel in "The Genus Aspergillus," The Williams and Wilkins Company, Baltimore, Md., 1965.

Color names were assigned according to the ISCC-NBS method (K. L. Kelly and D. B. Judd, "The ISCC-NBS Method of Designating Color and a Dictionary of Color Names," U.S. Dept. of Commerce, Circ. 553, Washington, D.C., 1955). The Maerz and Paul color blocks are described by A. Maerz and M. R. Paul in "Dictionary of Color," McGraw-Hill Book Company, New York, N.Y., 1950.

Cultures were grown at 25° C. unless otherwise specified.

Culture Characteristics of A. rugulosus NRRL 8113
Czapek's Solution Agar The culture grows slowly, attaining 1.5 to 2.0 cm in diameter in 15 days at 25° C. The colony surface is convex and velutinous, becoming wrinkled with age near the center and then umbonate. The mycelium periphery is a 2-mm wide band of deeply submerged colorless hyphae and is sinuate. A pinkish-brown exudate forms on the marginal aerial hyphae. In from 7 to 14 days a pale purple soluble pigment is produced in the agar surrounding the colony. The pigment diffuses throughout the colony by 15 days.

After 5 days the colony surface ranges from white to buff, and the colony reverse is brownish orange centrally and brownish to brownish purple in the peripheral regions. In 10 days the colony is moderate yellowish pink (ISCC-NBS 29 and Maerz and Paul II-A-7). After 14 days the colony is light grayish red (ISCC-NBS 18 and Maera and Paul 4-G-7). The marginal area becomes verruculose and is strong yellow (ISCC-NBS 84 and Maerz and Paul 10-L-5) due to conidiation. Scattered dull yellowish clusters of hulle cells occur randomly over the surface and along the margin of the colony. With age, the strong yellow patches and marginal area become yellowish green. After 3 weeks, an orange-purple tone is observed in the new aerial components of the margin. Initially, the colony reverse is slightly concave. As it matures, the colony flattens to the agar surface, and the reverse becomes slightly wrinkled. By 10 days the reverse is light brown (ISCC-NBS 57 and Maerz and Paul 5-A-10). In 15 days it is grayish red (ISCC-NBS 19 and Maerz and Paul 6-J-3).

The conidiogenous state is sparse; and conidiophores are scattered over the surface, sometimes occurring as patches or in a submarginal band. Conidial heads are at first loosely radiate and globose; with aging, they may develop as short columnar forms which are more compact. Globose heads are from 70$\mu$ to 80$\mu$ in diameter and average 50$\mu$. Columnar heads may be up to 140$\mu$ long and 70$\mu$ wide.

Conidia are globose to subglobose, rugulose, and greenish gold en masse. They range from 2.8$\mu$ to 3.9$\mu$ in diameter and average 3.2$\mu$.

Sterigmata are biseriate and colorless. Primary sterigmata range in length from 4.7$\mu$ to 11.0$\mu$ and average 7.9$\mu$. At their widest point they are 2.4$\mu$ and taper to 1.6$\mu$. Secondary sterigmata may occur singly or in pairs, arising from the primaries, and are flask shaped. At their widest point they measure 3.0$\mu$ and taper apically to 0.4$\mu$ where they become tubular. The tubular apex is 1.2$\mu$ long. The overall length ranges from 5.5$\mu$ to 12.6$\mu$ and averages 9.2$\mu$.

Vesicles are globose to subglobose or hemispherical and may be apically flattened, becoming brownish with age. They range from 7.4$\mu$ to 11.2$\mu$ in diameter and average 9.4$\mu$.

Conidiophores are smooth, relatively thick-walled, and are at first hyaline then evolve to a light cinnamon brown. They are slightly wider at the vesicle and may taper slightly near the foot cell. The average width is 5.9$\mu$. Conidiophores range from 47.7$\mu$ to 166.6$\mu$ and average 106$\mu$ in length. They arise from submerged hyphae or laterally from aerial hyphal filaments.

The ascogenous state appears in up to 20 days. The small yellowish clusters of hulle cells which occur on the surface may be found at any level in the mycelium. They consist of hulle cells which envelope one or more cleistothecia. Hulle cells are globose to subglobose or oval to elongate, are thick-walled and hyaline. Globose hulle cells range from 18$\mu$ to 24$\mu$ in diameter and average 21.8$\mu$.

Cleistothecia are globose to subglobose, thick-walled, relatively tough and fibrous. At first relatively colorless, they become reddish purple and darken with age. They measure from 165$\mu$ to 470$\mu$ in diameter and average 275$\mu$.

Malt Extract Agar

Colonies grown at 25° C. expand rapidly, attaining 4–5 cm in 10–12 days. At first a grayish white, colonies become moderate olive green (ISCC-NBS 90 and Maerz and Paul 23-E-6) in 4 days. The sinuate to weakly lobate periphery consists of tightly packed, short, white aerial hyphae. Small yellowish clusters of hulle cells dot the margin and are randomly scattered over the felt-like agar surface. After 20 days these hulle cell clusters tend to encrust much of the surface. The colony reverse in grayish yellow (ISCC-NBS 90 and Maerz and Paul 11-B-1).

The ascogenous state appears in 15 days. The small yellowish clusters of hulle cells which occur on the surface may be found at any level in the mycelium. They consist of hulle cells which envelope one or more cleistothecia. Hulle cells may encrust large areas over the conidial heads. Hulle cells are globose to subglobose or oval to elongate, are thick-walled and hyaline. Globose hulle cells range from 18$\mu$ to 24$\mu$ in diameter and average 21.8$\mu$.

Cleistothecia are globose to subglobose and are dark reddish brown. They range from 389$\mu$ to 700$\mu$ in diameter and average 506$\mu$.

Asci are fragile, hyaline, and subglobose to oval. Subglobose asci are from 8.7$\mu$ to 11.9$\mu$ in diameter and average $10.3\mu$. Oval asci are from $10.3\mu-14.2\mu \times 8.7\mu-10.3\mu$ and average $12.2\mu \times 9.1\mu$.

Ascospores are red-orange, rugulose, with two parallel, delicately pleated equatorial crests which are up to $0.8\mu$ wide and unbroken. The ascospore appears lenticular through the long axis. When the crest is peripheral, the ascospore is globose. In the globose view it is from $4.9\mu$ to $6.3\mu$ in diameter and averages $5.4\mu$.

Two characteristics of the A-30912-producing strain of *Aspergillus rugulosus* differ from the characteristics of *A. rugulosus* described by Raper and Fennel, supra. The A-30912-producing strain has larger conidial heads and ascospores.

The *Aspergillus rugulosus* culture useful for the production of the A-30912 antibiotic complex has been deposited and made a part of the stock culture collection of the Northern Regional Research Laboratory, U.S. Department of Agriculture, Agricultural Research Service, Peoria, Illinois 61604, from which it is available to the public under the number NRRL 8113.

Another organism which is useful for the preparation of antibiotic A-30912 factor A (antibiotic A-22082) is described in a copending application of Higgens and Michel titled ANTIBIOTIC A-22082 AND PROCESS FOR PRODUCTION THEREOF, Ser. No. 619,108, filed Oct. 2, 1975. This organism has also been deposited at the Northern Regional Research Laboratory and is available under the number NRRL 8112.

The culture medium employed to grow *Aspergillus rugulosus* NRRL 8113 can be any one of a number of media. For economy in production, optimal yield and ease of product isolation, however, certain culture media are preferred. Thus, for example, a preferred carbohydrate source in large-scale fermentation is glucose, although molasses, starch, lactose, sucrose, maltose, glycerol and the like may be employed. Preferred nitrogen sources are enzyme-hydrolyzed casein and soluble meat peptone, although distiller's grains, monosodium glutamate and the like may be used. Nutrient inorganic salts can be incorporated in the culture media. These include the customary soluble salts capable of yielding sodium, magnesium, calcium, ammonium, chloride, carbonate, sulfate, nitrate, and the like ions.

Essential trace elements necessary for the growth and development of the organism should also be included in the culture medium. Such trace elements commonly occur as impurities in other constituents of the medium in amounts sufficient to meet the growth requirements of the organism.

It may be necessary to add small amounts (i.e. 0.2 ml./l.) of an antifoam agent such as polypropylene glycol to large-scale fermentation media if foaming becomes a problem.

For production of a substantial quantity of the A-30912 antibiotic complex, submerged aerobic fermentation in tanks is preferred. Small quantities of the A-30912 antibiotic complex may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form of mycelial fragments of the organism to obtain a fresh, actively growing culture of the organism. The vegetative inoculum is then transferred to a larger tank. The medium used for the growth of the vegetative inoculum can be the same as that used for larger fermentations, but other media can also be employed. The A-30912-producing organism can be grown at temperatures between about 20° and about 43° C.; the organism grows well at temperatures of about 25°–30° C. Optimum production of the A-30912 antibiotic complex appears to occur at a temperature of about 25° C.

As is customary in aerobic submerged culture processes, sterile air is blown through the culture medium. For efficient antibiotic production, the volume of air employed in tank production is preferably above 0.4 volume of air per volume of culture medium per minute (V/V/M).

Production of the A-30912 antibiotic complex can be followed during the fermentation by testing samples of alcoholic extracts of the whole broth for antibiotic activity against an organism known to be sensitive to the A-30912 antibiotics. One assay organism useful in testing for the presence of the A-30912 antibiotic complex is *Candida albicans*. The bioassay is conveniently performed by paper-disc assay on seeded agar plates.

Generally, antibiotic activity can be detected on the second day of fermentation. Maximum production of antibiotic activity usually occurs between about the third and the sixth days.

The A-30912 antibiotic factors are antifungal agents. Illustrative of the antifungal activity of the A-30912 factors are in vitro tests with A-30912 factors A and D. These tests are summarized in Table III. Antifungal activity was measured by the conventional disc-diffusion method (6mm pads were dipped in solutions containing test compound; pads were placed on agar plates seeded with the test organism). Results are given as the minimal inhibitory concentration (MIC) per disc at which the test compound inhibited the test organism.

TABLE III

| Test Organism | MIC (mcg/disc) | |
|---|---|---|
| | A-30912 Factor A | A-30912 Factor D |
| Candida albicans | 0.625 | 0.5 |
| Trichophyton mentagrophytes | 0.078 | 0.07 |

A-30912 factor A is very active in vitro disc-diffusion tests against dermatophytes. The results of these tests are summarized in Table IV.

TABLE IV

| A-30912 FACTOR A VS. DERMATOPHYTES | | |
|---|---|---|
| Dermatophyte | No. of Isolates | MIC(mcg/disc) |
| Trichophyton mentagrophytes | 13 | 1.25 – 0.39 |
| Trichophyton gallinae | 1 | >1.25 |
| Trichophyton meginini | 1 | 0.0195 |
| Trichophyton quinckeanum | 1 | >1.25 |
| Trichophyton rubrum | 1 | <.0098 |
| Trichophyton schoenleinii | 1 | 0.0195 |
| Trichophyton terrestre | 1 | 0.0195 |
| Trichophyton tonsurans | 9 | >1.25 – 0.156 |
| Microsporium gypseum | 5 | 0.156 – 0.038 |
| Microsporium audouinii | 4 | 1.25 – 0.156 |
| Microsporium canis | 6 | 1.25 – 0.0098 |
| Microsporium cookei | 2 | 1.25 – 0.0195 |
| Nannizzia incurvata | 1 | 0.312 |

TABLE IV-continued
A-30912 FACTOR A VS. DERMATOPHYTES

| Dermatophyte | No. of Isolates | MIC(mcg/disc) |
|---|---|---|
| Phalaphere jean salemi | 1 | >1.25 |
| Epidermatophyton floccosum | 1 | 1.25 |
| Geotrichum candidum | 4 | >1.25 – 0.156 |
| Keratinomyces ajellio | 1 | 0.156 |

The antifungal activity of the A-30912 antibiotic factors was further demonstrated by in vivo tests. The in vivo tests were carried out in the following manner: Three doses of test compound are given to Candida albicans-infected mice at 0, 4, and 24 hours post-infection. The protection which the test compound provides is measured as an $ED_{50}$ value [the effective dose in mg/kg which protects 50 percent of the mice; see W. Wick et al., J. Bacteriol. 81, 233–235 (1961)]. The $ED_{50}$ values for A-30912 factor A against Candida albicans in mice were 30 mg/kg (intraperitoneal administration) and 50 mg/kg (subcutaneous administration). The $ED_{50}$ value for A-30912 factor D against Candida albicans in mice was 33 mg/kg (subcutaneous administration).

There were no signs of acute toxicity when A-30912 factor A was administered intraperitoneally (ip) or subcutaneously (sc) to mice at 100 mg/kg twice per day for three days (a total of 600 mg/kg). There were also no signs of acute toxicity when A-30912 factor A was administered ip to mice at 200 mg/kg three times per day (a total dose of 600 mg/kg).

There were no signs of acute toxicity when A-30912 factor D was administered sc to mice three times per day at 14 mg/kg (a total dose of 42 mg/kg).

When used as antifungal agents, the A-30912 antibiotic factors are administered parenterally and are commonly administered together with a pharmaceutically-acceptable carrier or diluent. The dosage of antibiotic A-30912 factor will depend upon a variety of conditions, such as the nature and severity of the particular infection involved.

In order to illustrate more fully the operation of this invention, the following examples are provided.

EXAMPLE 1

A. Shake-flask Fermentation

A culture of Aspergillus rugulosus NRRL 8113 was prepared and maintained on an 18- × 150- ml agar slant having the following composition:

| Ingredient | Amount (percent) |
|---|---|
| Dextrin | 1.0000 |
| Enzymatic hydrolystate of casein* | 0.2000 |
| Yeast extract | 0.1000 |
| Beef extract | 0.1000 |
| KCl | 0.0200 |
| $MgSO_4 \cdot 7H_2O$ | 0.0200 |
| $FeSO_4 \cdot 7H_2O$ | 0.0004 |
| Water | 98.5596 |

*N-Z-Amine A, Sheffield Chemical Co., Norwich, N.Y.

The slant was inoculated with Aspergillus rugulosus NRRL 8113, and the inoculated slant was incubated at 25° C. for about 7 days. The mature slant culture was covered with beef serum and scraped with a sterile loop to loosen the spores. One-half of the resulting suspension was used to inoculate 50 ml of a vegetative medium having the following composition:

| Ingredient | Amount (Percent) |
|---|---|
| Sucrose | 2.5 |
| Molasses | 3.6 |
| Corn steep liquor | 0.6 |
| Enzymatic hydrolystate of casein* | 1.0 |
| $K_2HPO_4$ | 0.2 |
| Water | 92.1 |

*N-Z-Case, Sheffield Chemical Co., Norwich, N.Y.

The inoculated vegetative medium was incubated in a 250-ml wide-mouth Erlenmeyer flask at 25° C. for 24 hours on a shaker rotating through an arc two inches in diameter at 250 RPM.

This incubated vegetative medium may be used directly to inoculate the second-stage vegetative medium. Alternatively and preferably, it can be stored for later use by maintaining the culture in the vapor phase of liquid nitrogen. The culture is prepared for such storage in multiple small vials as follows: In each vial is placed 2 ml of incubated vegetative medium and 2 ml of a glycerol-lactose solution having the following composition:

| Ingredient | Amount |
|---|---|
| Glycerol | 20% |
| Lactose | 10% |
| Deionized water | 70% |

The prepared suspensions are stored in the vapor phase of liquid nitrogen.

A stored suspension (1 ml) thus prepared was used to inoculate 50 ml of a first-stage vegetative medium having the same composition earlier described for the vegetative medium. The inoculated first-stage vegetative medium was incubated in a 250-ml wide-mouth Erlenmeyer flask at 25° C for 22 hours on a shaker rotating through an arc 2 inches in diameter at 250 RPM.

B. Tank Fermentation

In order to provide a larger volume of inoculum, 10 ml of the above-described incubated first-stage vegetative medium was used to inoculate 400 ml of a second-stage vegetative growth medium having the same composition as that of the vegetative medium. The second-stage medium was incubated in a 2-liter wide-mouth Erlenmeyer flask at 25° C for 25 hours on a shaker rotating through an arc 2 inches in diameter at 250 RPM.

Incubated second-stage vegetative medium (800 ml), prepared as above-described, was used to inoculate 100 liters of sterile production medium having the following composition:

| Ingredient | Amount |
|---|---|
| Glucose | 25 g/liter |
| Starch | 10 g/liter |
| Peptone* | 10 g/liter |
| Blackstrap molasses | 5 g/liter |
| Enzymatic hydrolysate of casein** | 4 g/liter |
| $MgSO_4 \cdot 7H_2O$ | 0.5 g/liter |
| Czapek's mineral stock*** | 2.0 ml/liter |
| $CaCO_3$ | 2.0 g/liter |

-continued

| Ingredient | Amount |
|---|---|
| Deionized water | q.s. 1 liter |

*W.P. No. 159, Inolex Biomedical Corp., Glenwood, Ill.
**N-Z Amine A, Sheffield Chemical Co., Norwich, N.Y.
***Czapek's mineral stock has the following composition:

| Ingredient | Amount |
|---|---|
| $FeSO_4 \cdot 7H_2O$ (dissolved in 2 ml conc HCl) | 2 g |
| KCl | 100 g |
| $MgSO_4 \cdot 7H_2O$ | 100 g |
| Deionized water | q.s. to 1 liter |

The pH of the medium was 6.8 after sterilization by autoclaving at 121° C for 30 min at about 16–18 pounds pressure. The inoculated production medium was allowed to ferment in a 165-liter fermentation tank at a temperature of 25° C for 4 days. The fermentation medium was aerated with sterile air at the rate of 0.5 V/V/M. The fermentation medium was stirred with conventional agitators at 300 RPM.

EXAMPLE 2

Separation of the A-30912 Antibiotic Complex

Whole fermentation broth (200 l.), obtained by the method described in Example 1, was stirred thoroughly with methanol (200 l.) for 1 hour and then was filtered, using a filter aid (Hyflo Super-cel, a diatomaceous earth, Johns-Manville Products Corp.). The pH of the filtrate was adjusted to pH 4.0 by the addition of 5 N HCl. The acidified filtrate was extracted twice with equal volumes of chloroform. The chloroform extracts were combined and concentrated under vacuum to a volume of about 4 liters. This concentrate was added to about 60 liters of diethyl ether to precipitate the A-30912 complex. The precipitate was separated by filtration and dried to give 38 g of the A-30912 antibiotic complex as a gray powder. The filtrate was concentrated under vacuum to give an oil; this oil was dissolved in methanol (500 ml). The methanol solution was added to diethyl ether (7.5 l.) to precipitate additional A-30912 complex. This precipitate was also separated by filtration and dried to give and additional 3.5 g of the A-30912 antibiotic complex.

EXAMPLE 3

Isolation of A-30912 Factor A

A-30912 antibiotic complex (20 g), obtained as described in Example 2, was placed on a silica-gel column (4- × 107-cm, Woelm) in acetonitrile:water (95:5). The column was eluted with acetonitrile:water (95:5) at a flow rate of 1 to 2 ml per minute, collecting fractions having a volume of approximately 20 ml. Fractions were checked by thin-layer silica-gel chromatography, using the acetonitrile:water (95:5) solvent system and *Candida albicans* bioautography.

Fractions 74 through 125 were combined and concentrated. The concentrated solution crystallized upon standing to give an additional 124 mg of sterigmatocystin. Fractions 212 through 273 were combined and concentrated under vacuum to give an oil. This oil was dissolved in a small volume of methanol. The methanol solution was added to diethyl ether (15 volumes). The precipitate which formed was separated and dried to give 23 mg of A-30912 factor D. Fractions 274 through 437 contained A-30912 factors A, B, C and D. Fractions 482 through 900 contained A-30912 factors A, E, F and G. Fractions 438 through 481 were combined and concentrated under vacuum to give an oil. This oil was dissolved in a small volume of methanol; and the methanol solution was added to diethyl ether (15 volumes). The precipitate which formed was separated and dried to give 2.17 g of antibiotic A-30912 factor A.

EXAMPLE 4

Isolation of A-30912 Factor D

A partially purified A-30912 antibiotic complex containing A-30912 factors B, C, and D was obtained as described in Example 3 for fractions 274–437. This material (750 mg) was chromatographed on a silica-gel column (2.2 × 51 cm, Woelm silica gel), collecting fractions having a volume of approximately 15 ml and eluting with the following solvents:

| Fractions | Solvent |
|---|---|
| 1–25 | acetonitrile |
| 26–62 | acetonitrile + 1% water |
| 63–700 | acetonitrile + 1.5% water |

The column fractions were monitored by silica-gel thin-layer chromatography, using acetonitrile:water (95:5) and benzene:methanol (7:3) solvent systems and *Candida albicans* bioautography. Fractions 535–685, which contained A-30912 factor D, were combined and concentrated under vacuum to give an oil. This oil was dissolved in a small amount of methanol and added to diethyl ether (15 volumes). The precipitate which formed was separated by filtration and dried to give 69 mg of A-30912 factor D.

EXAMPLE 5

Isolation of A-30912 factors B and C

Partially purified A-30912 antibiotic complex containing A-30912 factors A, B, C, and D was obtained as described in Example 3 for fractions 212–437. This material (18 g) was dissolved in a minimal volume of acetonitrile:water (4:1) and chromatographed on an aluminum oxide column (3.8 × 56 cm, Woelm), collecting fractions having a volume of approximately 20 ml. The column was eluted with the following solvents:

| Fractions | Solvent |
|---|---|
| 1–300 | acetonitrile:water (4:1) |
| 301–509 | acetonitrile:water (7:3) |

The column fractions were monitored by silica-gel thin-layer chromatography as described in Example 4. On the basis of these results, fractions were combined and concentrated to oils; the oily residues were dissolved into small volumes of methanol; the methanol solutions were precipitated with 10–15 volumes of diethyl ether. The manner in which the fractions were combined, the weight of material obtained, and the factor content of the combined fractions are summarized below.

| Fraction | Weight (g) | Factors |
|---|---|---|
| 6–28 | 0.23* | — |
| 6–28 | 5.80 | A-30912 C, D |
| 34–114 | 2.90 | A-30912 B |
| 115–164 | 1.20 | A-30912 A, B |
| 165–509 | 1.90 | A-30912 A |

*insoluble material obtained before ether precipitation

In order to obtain purified A-30912 factor C, a portion of fractions 6–28 (2 g) was dissolved in methanol, adsorbed onto a sufficient quantity of silica gel (grade 62), dried, and added on the top of a silica-gel column (1.9 × 80 cm, grade 62), packed in acetonitrile. The column was eluted with acetonitrile at a flow rate of 2 ml/minute, collecting factions having a volume of about 10 ml. At fraction 117, the solvent was changed to acetonitrile:water (99:1 ). The column fractions were again monitored by thin-layer chromatography. On the basis of the TLC results, fractions were combined and concentrated to give oily residues; the oily residues were dissolved into a small volumes of methanol; the methanol solutions were precipitated with 10–15 volumes of diethyl ether. The factor content and weight of the fractions of interest are summarized below:

| Fractions | Weight (g) | Factors |
|---|---|---|
| 341–479 | 0.250 | D |
| 480–540 | 0.015 | D |
| 541–899 | 0.391 | C, D |
| 900–1675 | 0.340 | C |

We claim:
1. Antibiotic A-30912 factor D which is a white amorphous solid; which is soluble in methanol, ethanol, dimethylformamide, dimethyl sulfoxide, or ethyl acetate and in aqueous solutions having a pH greater than 7.0; but which is insoluble in diethyl ether or petroleum ether; and which has:
   a. an approximate molecular weight of 1100;
   b. an approximate elemental composition of 56.37 percent carbon, 8.17 percent hydrogen, 8.54 percent nitrogen, and 26.92 percent oxygen (by difference);
   c. the following specific rotation:

$$[\alpha]_D^{25} - 50° \ (c\ 0.34,\ CH_3OH);$$

d. an infrared absorption spectrum in KBr disc with the following observable characteristic absorption maxima: 2.98 (strong), 3.31 (weak), 3.36 (shoulder), 3.40 (medium), 3.48 (weak), 5.76 (weak), 6.01 (strong), 6.10 (shoulder), 6.49 (medium), 6.57 (medium), 6.90 (medium), 7.81 (weak), 8.07 (weak), and 9.16 (weak) microns;
   e. ultraviolet absorption spectra in both neutral and acidic methanol with absorption maxima at 225 nm ($\epsilon$ 18,000) and 275 nm ($\epsilon$ 2,500) and in basic methanol with absorption maxima at 240 nm ($\epsilon$ 11,000) and 290 nm ($\epsilon$ 3,000);
   f. an amino-acid analysis, after hydrolysis, which indicates the presence of threonine, hydroxyproline, histidine, and three other as-yet-unidentified amino acids; and
   g. an $R_f$ value of 0.59 on silica-gel thin-layer chromatography using a benzene: methanol (7:3) solvent system and Candida albicans bioautography for detection.

2. Antibiotic A-30912 factor B which is a white amorphous solid; which is soluble in methanol, ethanol, dimethylformamide, dimethyl sulfoxide, or ethyl acetate and in aqueous solutions having a pH greater than 7.0; but which is insoluble in diethyl ether or petroleum ether; and which has:
   a. an approximate elemental composition of 57.36 percent carbon, 5.92 percent hydrogen, 8.75 percent nitrogen, and 26.19 percent oxygen;
   b. an infrared absorption spectrum in KBr disc with the following observable characteristic absorption maxima: 2.99, 3.41, 3.49, 6.06, 6.15, 6.54, 6.61, 6.94, 7.62, 8.07, 9.26, and 9.39 microns;
   c. ultraviolet absorption spectra in both neutral and acidic methanol with absorption maxima at 223 nm (shoulder, $\epsilon$ 16,000) and 278 nm ($\epsilon$ 2,400) and in basic methanol with absorption maxima at 242 nm ($\epsilon$ 13,900) and 292 nm ($\epsilon$ 2,800);
   d. the following approximate specific rotations:

$$[\alpha]_D^{25} -47° \ (c\ 0.5,\ CH_3OH)$$
$$[\alpha]_{365}^{25} - 170° \ (c\ 0.5,\ CH_3OH);$$

e. a titratable group with a $pK_a$ value of about 13.0 in 66% aqueous dimethylformamide;
   f. an $R_f$ value of 0.45 on silica-gel thin-layer chromatography using a benzene:methanol (7:3) solvent system and Candida albicans bioautography for detection; and
   g. after standard acid hydrolysis, an amino-acid analysis which indicates the presence of threonine, hydroxyproline, and several as-yet-unidentified amino acids.

3. Antibiotic A-30912 factor C which is a white amorphous solid; which is soluble in methanol, ethanol, dimethylformamide, dimethyl sulfoxide, or ethyl acetate and in aqueous solutions having a pH greater than 7.0; but which is insoluble in diethyl ether or petroleum ether; and which has:
   a. an approximate elemental composition of 56.76 percent carbon, 7.88 percent hydrogen, 10.61 percent nitrogen, and 25.09 percent oxygen;
   b. an infrared absorption spectrum in KBr disc with the following observable characteristic absorption maxima: 2.98, 3.39, 3.43, 3.51, 6.01, 6.12, 6.47, 6.90, 7.04, 7.22, 7.38, 8.00, 8.30, and 9.13 microns;
   c. ultraviolet absorption spectra in both neutral and acidic methanol with absorption maxima at 223 nm (shoulder, $\epsilon$ 7,300) and 275 nm ($\epsilon$ 1,350) and in basic methanol with absorption maxima at 240 nm ($\epsilon$ 12,400) and 290 nm ($\epsilon$ 5,200);
   d. the following approximate specific rotations:

$$[\alpha]_D^{25} - 33° \ (c\ 0.5,\ CH_3OH)$$
$$[\alpha]_{365}^{25} -119° \ (c\ 0.5,\ CH_3OH);$$

e. a titratable group with a $pK_a$ value of about 13.08 in 66% aqueous dimethylformamide;
   f. an $R_f$ value of 0.54 on silica-gel thin-layer chromatography using a benzene:methanol (7:3) solvent system and Candida albicans bioautography for detection; and
   g. after standard acid hydrolysis, an amino-acid analysis which indicates the presence of threonine, hydroxyproline, and several as-yet-unidentified amino acids.

4. The method of producing the A-30912 antibiotic complex comprising A-30912 factor D as defined in claim 1, A-30912 factor B, A-30912 factor C, and A-30912 factor A, white amorphous solid, which is soluble in methanol, ethanol, dimethylformamide, dimethyl sulfoxide, ethyl acetate or in aqueous solutions having a pH greater than 7.0; but which is insoluble in diethyl ether or petroleum ether; and which has:
   a. an approximate molecular weight of 1100, as determined by mass spectrometry and titration;
   b. an approximate elemental composition of 56.52 percent carbon, 7.29 percent hydrogen, 8.68 percent nitrogen, and 27.09 percent oxygen;
   c. an approximate empirical formula of $C_{51-53}H_{79-83}N_7O_{17-19}$;
   d. the following specific rotations:

$[\alpha]_D^{25}$ —to 44° (c 0.5, $CH_3OH$)
   $[\alpha]_{365}^{25}$ —156° (c 0.5, $CH_3OH$)

e. an infrared absorption spectrum in KBr disc with the following observable characteristic absorption maxima: 2.97 (strong), 3.39 (medium), 3.47 (weak), 5.99 (strong), 6.10 (strong), 6.49 (medium), 6.56 (medium), 6.90 (medium), 8.00 (weak), 9.13 (weak), and 11.77 (weak) microns;
   f. ultraviolet absorption spectra in both neutral and acidic methanol with absorption maxima at 225 nm ($\epsilon$ 18,000), 275 nm ($\epsilon$ 3,000) and 284 nm (shoulder $\epsilon$ 2,500) and absorption maxima in basic methanol at 245 nm ($\epsilon$ 16,000) and 290 nm ($\epsilon$ 3,000);
   g. a $^{13}C$ nuclear magnetic resonance spectrum in perdeuteromethanol with the following characteristics: δ 176.1, 174.3, 173.4, 172.7, 172.4, 169.8, 158.4, 132.8, 130.9, 129.6, 129.0, 116.2, 77.0, 75.7, 74.4, 71.3, 70.9, 69.6, 68.3, 62.4, 58.7, 56.9, 56.1, 52.9, 39.0, 38.5, 36.8, 35.2, 33.9, 32.9, 32.6, 30.7, 30.4, 30.2, 28.2, 27.0, 26.5, 23.6, 20.1, 19.6, 14.4, and 11.3 ppm;
   h. a titratable group with a $pK_a$ value of 12.7 in 66% aqueous dimethylformamide;
   i. after hydrolysis, an amino-acid analysis which indicates the presence of threonine, hydroxyproline, and three other as-yet-unidentified amino acids;
   j. an $R_f$ value of 0.35 on silica-gel thin-layer chromatography using a benzene-methanol (7:3) solvent system and *Candida albicans* bioautography for detection;
   k. the following $R_f$ values in the paper-chromatographic systems indicated below, using Candida albicans bioautography for detection:

| $R_f$ Value | Solvent System |
|---|---|
| 0.76 | Butanol saturated with water |
| 0.69 | Butanol saturated with water plus 2% p-toluenesulfonic acid |
| 0.75 | Methanol:0.1 N HCl (3:1) |
| 0.17 | Butanol:ethanol:water (13.5:15:150) |
| 0.78 | Methanol:0.05 M sodium citrate at pH 5.7 (7:3); paper buffered with 0.05 M sodium citrate at pH 5.7 | which method comprises cultivating *Aspergillus rugulosus* NRRL 8113 in a culture medium containing assimilable sources of carbohydrate, nitrogen, and inorganic salts under submerged aerobic fermentation conditions until a substantial amount of antibiotic activity is produced by said organism in said culture medium.

5. The method of claim 4 which includes the additional step of separating the A-30912 antibiotic complex from said culture medium.

6. The method of claim 5 which includes the additional step of isolating A-30912 factor A from the separated A-30912 antibiotic complex.

7. The method of claim 5 which includes the additional step of isolating A-30912 factor D from the separated A-30912 antibiotic complex.

8. The method of claim 5 which includes the additional step of isolating A-30912 factor B from the separated A-30912 antibiotic complex.

9. The method of claim 5 which includes the additional step of isolating A-30912 factor C from the separated A-30912 antibiotic complex.

* * * * *

Notice of Adverse Decision in Interference

In Interference No. 100,071, involving Patent No. 4,024,245, M. M. Hoehn and K. H. Michel, ANTIBIOTIC A-30912 AND PROCESS FOR PRODUCTION THEREOF, final judgment adverse to the patentees was rendered July 20, 1981, as to claims 1 and 2.

[*Official Gazette November 3, 1981.*]